United States Patent [19]
Linke et al.

[11] 3,981,987
[45] Sept. 21, 1976

[54] HAIR SETTING COMPOSITIONS CONTAINING EASILY REMOVABLE NEUTRALIZED COPOLYMERS

[75] Inventors: Wolfgang Linke; Karl Herrle; Wolfgang Schwarz, all of Ludwigshafen; Johannes Perner, Neustadt, all of Germany

[73] Assignee: BASF Aktiengesellschaft, Ludwigshafen (Rhine), Germany

[22] Filed: Jan. 8, 1975

[21] Appl. No.: 539,417

[30] Foreign Application Priority Data
Feb. 1, 1974 Germany............................ 2404793

[52] U.S. Cl................................. 424/47; 8/127.51; 260/29.6 ME; 260/29.6 N; 260/29.6 TA; 260/33.4 R; 260/33.8 R; 260/78.4; 424/DIG. 1; 424/DIG. 2; 424/71; 424/78; 424/81; 526/14; 526/15; 526/49; 526/50; 526/318; 526/325
[51] Int. Cl.$^2$............................................ A61K 7/11

[58] Field of Search................. 424/DIG. 1, DIG. 2, 424/47, 71, 78, 81; 260/78.4 E, 78.5 T, 29.6 TA, 29.6 N, 29.6 ME, 33.4 R, 33.8 R; 8/127.51

[56] References Cited
UNITED STATES PATENTS
3,810,977   5/1974   Levine et al........................... 424/47

*Primary Examiner*—James O. Thomas, Jr.
*Assistant Examiner*—Vera C. Clarke
*Attorney, Agent, or Firm*—Johnston, Keil, Thompson & Shurtleff

[57] ABSTRACT

Copolymers obtained by copolymerization of vinyl esters of aliphatic carboxylic acids and/or acrylic or methacrylic acid esters of aliphatic alcohols, with half-esters of ethylenically unsaturated dibasic carboxylic acids, followed by neutralization with bases, are used in hair setting compositions.

10 Claims, No Drawings

HAIR SETTING COMPOSITIONS CONTAINING EASILY REMOVABLE NEUTRALIZED COPOLYMERS

This invention relates to copolymers for use in hair setting compositions.

It is known that natural or synthetic resins, generally in aqueous-alcoholic or alcoholic solution, can be used as hair lacquers, as wavesetting lotions and, in conjunction with propellants, as hair sprays.

The purpose of using such resins in cosmetics is to fix the hair and improve its appearance, in particular to make it more lustrous.

Hitherto, film-forming resins which can be washed off with water, in particular homopolymers, such as polyvinylpyrrolidone, or copolymers of vinylpyrrolidone and vinyl acetate, acrylic acid esters and unsaturated lower aliphatic acids, maleic anhydride and alkyl vinyl ethers, which may contain ester or amide groups, and also copolymers of vinyl acetate and unsaturated lower aliphatic acids, such as crotonic acid, have been used for this purpose.

However, none of the products hitherto used have given entirely satisfactory results.

It is very difficult to achieve simultaneously all the various properties desired of a lacquer, wavesetting lotion or hair spray, since these properties are frequently contradictory. Thus, it is desirable to produce a durable film on the hair, which has improved luster, good setting properties, adheres well and has no significant tendency to flake off. Moreover, the film on the hair should not be significantly hygroscopic, to avoid the hair appearing sticky. On the other hand, the lacquer must be readily removable, both by light brushing and by washing with water or any shampoo.

The conventional products represent an endeavour to find a compromise between the various properties desired, without it being possible to say that the products in fact exhibit all the desired properties to a satisfactory degree. In such products, certain properties have simply been favored at the expense of others. Thus there are polymers which are too readily water-soluble. It is true that such polymers do not flake off and can be removed very easily with water, but when the atmospheric humidity exceeds 60 to 70%, these polymers have the disadvantage of absorbing moisture, causing the hair to stick together very readily and appear unsightly.

Other, less hygroscopic resins tend to form white dandruff-like flakes which are objectionable and are difficult to remove with certain shampoos.

Furthermore, these resins do not make the hair as lustrous as is desired.

British Patent No. 1,041,910 has disclosed that copolymers which give better results in hair toiletries can be produced with certain half-esters of aliphatic dicarboxylic acids, such as maleic acid. These copolymers are terpolymers of maleic acid half-esters, vinyl acetate and crotonic acid.

However, a disadvantage which cannot be overcome by following the teaching of the said British patent is that such copolymers are contaminated with monomeric crotonic acid which has an unpleasant odor. Furthermore, such copolymers are often excessively hygroscopic since they are terpolymers containing two components which contain groups which become water-soluble on neutralization, namely the carboxyl group of the half-ester and the carboxyl group of crotonic acid.

It is an object of the present invention to provide hair setting compositions which do not suffer from the above shortcomings and which, when applied to the hair, give lustrous films which do not flake off, can be washed off with water and do not become sticky at high atmospheric humidity.

It is a further object of the invention to provide preparations which contain a film-forming resin soluble in water and organic solvents which, when applied to hair, is able to form lustrous, non-flaking films which can be washed off with water but are not sticky.

It is yet a further object of the present invention to provide copolymers, based on the said half-esters, which can be used to give hair setting compositions of all kinds which have been optimized in respect to insensitivity to humidity and ease of washing out and have all the other properties mentioned.

This object is achieved by using, as active ingredients in hair setting compositions, copolymers which contain the following copolymerized units (based on the weight of the copolymer):

a. from 20 to 95% by weight of one or more vinyl esters of aliphatic carboxylic acids of 2 to 20 carbon atoms and/or esters of acrylic acid and/or methacrylic acid with aliphatic alcohols of 1 to 6 carbon atoms and b. from 80 to 5% by weight of one or more half-esters of an ethylenically unsaturated dibasic carboxylic acid of 4 or 5 carbon atoms with aliphatic alcohols of 6 to 24 carbon atoms.

The copolymers are obtained by conventional methods of copolymerization of the said monomers in the presence of free radical initiators, followed by partial or complete neutralization with inorganic or organic bases.

The use of the said copolymers results in hair toiletries such as lotions or aerosol sprays, which show clearly improved properties without the disadvantages of the conventional preparations. In addition, the copolymers to be used according to the invention have the great advantage that they can be removed very easily by washing with non-ionic, anionic or cationic shampoos. Starting materials (a) for the copolymerization are, above all, the vinyl esters of aliphatic carboxylic acids of 2 to 20 carbon atoms, esters of acrylic acid and/or methacrylic acid with aliphatic alcohols of 2 to 6 carbon atoms, or mixtures of the said monomers. Examples of such monomers are vinyl acetate, vinyl propionate, vinyl pivalate and the vinyl esters of fatty acids of 10 to 20 carbon atoms, and also vinyl esters of branched carboxylic acids, e.g. of 8 to 10 carbon atoms.

Suitable acrylic acid esters and methacrylic acid esters which can be used as an alternative to the vinyl esters, or as mixtures with the latter, are, above all, the esters of lower aliphatic alcohols of 1 to 6 carbon atoms, preferably of 3 to 5 carbon atoms, such as isopropanol, isobutanol and tert.-butanol and above all cyclohexanol.

Suitable half-esters (b) are, above all, half-esters of maleic acid, fumaric acid, citraconic acid, mesaconic acid and itaconic acid with alcohols such as, in general, cyclohexanol or fatty alcohols of 6 to 24 carbon atoms, preferably of 10 to 20 carbon atoms. These alcohols may be of natural origin, e.g. coconut fatty alcohols, or of synthetic origin, such as, e.g., the so-called Ziegler alcohol cuts or the higher alcohols obtained by oxo reaction. The alcohols need not be single substances; it is possible to use technical fractions, for example the Ziegler alcohol fractions or oxo alcohol fractions of 9 to 11 carbon atoms, of 10 to 14 carbon atoms or of 18 to 20 carbon atoms. It is also possible to use mixtures of various half-esters, differing both in respect of the acid component and of the alcohol component, for the copolymerization.

For certain purposes, e.g. to modify the affinity of the polymers to hair, it may be advantageous to include further comonomers, which contain tertiary, protonized tertiary or quaternary nitrogen atoms in the molecule, in the copolymerization. Up to 10%, based on the weight of polymer, of such monomers may be present; examples are diethylaminoethyl acrylate or methacrylate, dimethylaminoethyl acrylate or methacrylate, or vinylimidazole.

In addition, minor amounts of other comonomers, such as styrene, vinyl chloride or acrylonitrile, may be present.

Particularly advantageous copolymers are obtained by the use of a mixture of a cyclohexyl half-ester and a mixed half-ester obtained from a fatty alcohol fraction of 10 to 14 carbon atoms, or of 16 to 18 carbon atoms, with maleic acid.

The copolymerization can be carried out in solution, in bulk (as a block polymerization) or in suspension, copolymerization in solution being most advantageous. If the solvent is suitably chosen, no further working up is required; residues of volatile monomers can be distilled off.

Solvents to be used are above all those which are in any case present in the final compositions, e.g. isopropanol, ethanol or ethylglycol.

In other respects, the polymerization is carried out by conventional methods in the presence of free radical initiators and optionally of regulators, at temperatures of from 50° to 120°C, at atmospheric pressure or pressures of up to 10 atmospheres gauge. Particularly favorable results are obtained if the polymerization is so controlled, following the conventional rules of polymerization technology, that copolymers of as homogeneous a composition as possible are produced, i.e. so that the individual polymer molecules contain the monomers concerned in the same ratio.

An example of a suitable method is to measure the electrical resistance continuously during the polymerization; this makes it possible to establish exactly whether too much or too little of the constituent containing carboxyl groups is present in the polymerization charge; if the deviations thus found are counterbalanced by reducing or increasing the slow addition of the half-ester (b), copolymers of substantially homogeneous structure are obtained.

According to the invention, from 20 to 95% by weight, preferably from 30 to 85% by weight, of component (a) and from 80 to 5% by weight, preferably from 70 to 15% by weight, of component (b) are used. The copolymers thus obtained have relative viscosities (measured on a 1% strength solution in isopropanol at 20°C) of from 1.0 to 1.5, and K values of approx. from 24 to 30.

To enable the copolymers to be used in the compositions mentioned, they are fully or partially neutralized with inorganic or organic bases so as to render them soluble in water and in the above organic solvents as well as in halogenated hydrocarbons, such as are conventionally employed as propellants in aerosol sprays.

Bases, such as ammonia, diethylamine, dimethylamine, triethanolamine, triisopropanolamine, 2-amino-2-methylpropanol or 1,2-amino-2-methyl-1,3-propanediol can be used, as already disclosed in the literature, to neutralize the copolymers.

An equimolar amount of bases (based on the amount of half-ester units in the copolymers) can be used for the neutralization reaction. However, the amount of base used can also be from 10 to 150% by weight of the calculated theoretical amount without impairing the result, i.e. the amount can, in principle, be varied within wide limits.

The stated ratios of the components (a) and (b) can be chosen in accordance with the particular desired mode of action of the composition.

The situation as described in the art (cf. in particular German Published Application No. 1,645,082) is that when the amount of substance containing carboxyl groups is reduced, the salt of the polymer becomes less soluble in water or alcohol, so that the possible applications of the substance are limited, and the substance is more difficult to remove by means of water. Conversely, if the proportion of monomeric substance containing carboxyl groups is increased excessively, the salt of the copolymer tends to become sticky because of its increased hygroscopicity.

If the proportion of water-insoluble monomer (component (a) is increased, the copolymer becomes more difficult to remove as it becomes water-soluble. Conversely, reducing the proportion of insoluble monomer reduces the luster and stability of the film on the hair.

In the copolymers to be used according to the invention, the proportion of monomers (a) and (b) can be varied widely within the claimed limits, without adversely changing the properties of the copolymers. Whilst varying the ratio usually produces a change in the character of the treated hair even in the case of the copolymers of the invention, the copolymers can in every case easily be washed off the hair, and the luster of the hair is unimpaired. This is a surprising technical advance, especially in the light of British Patent No. 1,041,910 which provides the terpolymer of vinyl acetate, crotonic acid and a half-ester of maleic acid referred to above.

The polymers of the invention can be used to manufacture a great variety of hair setting compositions. For example, the composition may be a hair lacquer obtained by dissolving one or more salts of the copolymers in an alcohol. This alcoholic solution, mixed with a liquefied propellant gas, can be kept under pressure in an aerosol can. For example, a hair lacquer aerosol can be obtained, according to the invention, by adding from 1 to 4 per cent by weight, based on the total mixture, of one or more salts of the copolymers of the invention to a mixture of from 25 to 60 parts by weight of an anhydrous aliphatic alcohol, e.g. ethanol or isopropanol, and from 40 to 75 parts by weight of a propellant gas or propellant gas mixture based on fluorinated hydrocarbons.

The composition can also consist of a wavesetting lotion obtained by dissolving from 1 to 4 per cent by weight, based on the solvent, of a salt or of a mixture of salts of the said copolymers, in from 20 to 50% strength ethanol or isopropanol. Of course, the compositions can contain additives such as softeners, scents, dyes and other conventional cosmetic adjuvants. Detailed instances of these are to be found in the Examples which follow.

The copolymers of the invention are easily removable by brushing and washing and do not tend to flake off the hair to which they have been applied.

The Examples which follow illustrate the manufacture of the copolymers and also demonstrate the technical advance achieved relative to British Patent No. 1,041,910.

EXAMPLE 1

A copolymer of 74% of vinyl acetate, 11.4% of the maleic acid half-ester of an Alfol of 12 to 14 carbon atoms and 14.6% of the maleic acid half-ester of cyclohexanol.

740 parts of vinyl acetate and 60 parts of isopropanol were heated in a stirred kettle, equipped with a reflux condenser, until the mixture boiled gently (about 70°C). 30 parts of a mixture of 114 parts of a half-ester of maleic acid with an alcohol of 12 to 14 carbon atoms, 146 parts of maleic acid cyclohexanol half-ester, 250 parts of isopropanol and 3 g of azidiisobutyronitrile were then added all at once, whilst the remainder of the mixture was run in uniformly in the course of 6 hours, during which the boiling point rose to 83°C. A further 2 parts of azodiisobutyronitrile were then added and the batch was kept at the boil for a further 2 hours and diluted with isopropanol, to lower the temperature to approx. 65°C, before being allowed to cool.

The solution obtained was completely clear and colorless. A 1% strength solution of the polymer in isopropanol had a relative viscosity of 1.32. A 20% strength solution of the polymer was slightly turbid at 20°C but cleared on warming to 25°C.

EXAMPLE 2

120 parts of ethanol and 100 parts of maleic acid cyclohexyl half-ester were heated to the boil (approx. 80°C) in a stirred kettle equipped with a reflux condenser. At this stage, a mixture of 150 parts of methyl methacrylate, 150 parts of methyl acrylate and 2 parts of azodiisobutyronitrile was added. The remainder of the mixture was run in uniformly in the course of 2 hours. The polymerization was then completed by boiling gently for a further 3 hours and the mixture was then diluted with 245 parts of ethanol.

A clear, viscous solution was obtained, which left a tough, non-tacky film on drying. A 1% strength solution of the polymer in cyclohexanone had a relative viscosity of 1.28.

EXAMPLE 3

A copolymer of 37.5 parts of methyl methacrylate, 32.5 parts of methyl acrylate, 5 parts of dimethylaminoethyl methacrylate and 25 parts of the cyclohexyl half-ester of maleic acid was prepared analogously to Example 1.

EXAMPLE 4

A copolymer of 30% of vinyl acetate and 70% of the maleic acid half-ester of an alfol of 12 to 14 carbon atoms was prepared analogously.

EXAMPLE 5

A copolymer of 77% of vinyl acetate and 23% of the maleic acid half-ester of cyclohexanol was prepared in accordance with the instructions of Example 1.

COMPARATIVE EXAMPLE

A terpolymer composed of 84% of vinyl acetate, 8% of crotonic acid and 8% of the maleic acid half-ester of n-butanol was prepared in accordance with the instructions of Example 3 of British Patent No. 1,041,910.

EXAMPLE 6

The following standard recipe was used to prepare a hair setting composition:

3 parts of a copolymer prepared according to Example 1 and neutralized to the extent of 50% or 100% with 2-amino-2-methyl-1,3-propanediol (AMPD), 1 part of stearylamine. 5 ethylene oxide or 0.3 part of a polyethylene glycol of molecular weight 400 and 96 or 96.7 parts of 40 or 45% strength ethanol or of 40 or 45% strength isopropanol.

A further recipe was based only on 3 parts of the copolymer of Example 1 and 97 parts of one of the alcohol solutions mentioned. Films prepared in accordance with these recipes were only slightly hygroscopic. Films obtained from copolymers neutralized to the extent of 75% were also only slightly hygroscopic and absorbed at most 6% of water after 7 days' storage at 75% relative atmospheric humidity.

The films possessed an attractive luster and fixed the hair extremely well even at high atmospheric humidity. The films could readily be brushed off the hair. The remnants which persisted were hardly visible and were redissolved by the solvent of the hair spray when respraying the hair.

The films could be removed very successfully from the hair by using a commercially available (neutral or slightly alkaline) shampoo, leaving no detectable residues.

Similar results were obtained with recipes using copolymers from Examples 2 and 3. Here again, alcoholic solutions containing 3% of copolymer generally proved best.

EXAMPLE 7

To prepare an aerosol hair lacquer, a solution of the copolymer prepared according to Example 1, 2 or 3 in alcohol or isopropanol was neutralized to the extent of from 50 to 100% with AMPD and packaged in aerosol cans together with $CCl_3F$ or $CCl_2F_2$ or butane and optionally together with methylene chloride or ethylglycol. Typical recipes are shown in the tables which follow, in which all the numerical data are percentages.

TABLE 1

| Copolymer according to Example 1, 50% neutralized | 3 | 3 | 3 | 3 | 3 | 3 | 3 | 3 | 3 |
|---|---|---|---|---|---|---|---|---|---|
| Isopropanol or ethyl alcohol | 17 | 27 | 47 | 3 | 11 | 3 | 45 | 3 | 3 |
| $CH_2Cl_2$ | | | 10 | 16 | 6 | 59 | 17 | 16 | 57 |
| Ethylglycol | | | | | | | | 2 | 2 |
| $CCl_3F+CCl_2F_2$ | 80 | 70 | | 78 | 80 | | | 76 | |
| Butane | | | 40 | | | 35 | 35 | | 35 |

TABLE 2

| Copolymer according to Example 1, 100% neutralized | 3 | 3 | 3 | 3 | 3 | 3 | 3 | 3 | 3 |
|---|---|---|---|---|---|---|---|---|---|
| Isopropanol or ethyl alcohol | 17 | 27 | 47 | 3 | 11 | 3 | 45 | 3 | 3 |
| $CH_2Cl_2$ | | | 10 | 21 | 6 | 59 | 17 | 21 | 57 |
| Ethylglycol | | | | | | | | 2 | 2 |
| $CCl_3F+CCl_2F_2$ | 80 | 70 | | 73 | 80 | | | 71 | |
| Butane | | | 40 | | | 35 | 35 | | 35 |

TABLE 3

| Copolymer according to Example 2, 50% neutralized | 3 | 3 | 3 | 3 | 3 | 3 | 3 | 3 | 3 |
|---|---|---|---|---|---|---|---|---|---|
| Isopropanol or ethyl alcohol | 17 | 27 | 47 | 3 | 11 | 3 | 51 | 3 | 3 |
| $CH_2Cl_2$ | | | 10 | 6 | 6 | 54 | 6 | 6 | 52 |
| Ethylglycol | | | | | | | | 2 | 2 |
| $CCl_3F+CCl_2F_2$ | 80 | 70 | | 88 | 80 | | | 86 | |
| Butane | | | 40 | | | 40 | 40 | | 40 |

TABLE 4

| Copolymer according to Example 2, 100% neutralized | 3 | 3 | 3 | 3 | 3 | 3 | 3 | 3 | 3 |
|---|---|---|---|---|---|---|---|---|---|
| Isopropanol or ethyl alcohol | 17 | 27 | 47 | 3 | 11 | 3 | 51 | 3 | 3 |
| $CH_2Cl_2$ | | | 10 | 6 | 6 | 54 | 6 | 6 | 52 |
| Ethylglycol | | | | | | | | 2 | 2 |
| $CCl_3F+CCl_2F_2$ | 80 | 70 | | 88 | 80 | | | 86 | |
| Butane | | | 40 | | | 40 | 40 | | 40 |

EXAMPLE 8

To prepare an aerosol hair lacquer, a solution of the copolymer prepared according to Example 5 in alcohol or isopropanol was neutralized as described under Example 7 and the adjuvants mentioned there were added. Table 5 shows some typical examples using the 50% neutralized copolymer and Table 6 some typical examples with the copolymer 100% neutralized with AMPD.

TABLE 5

| Copolymer according to Example 3, 50% neutralized | 3 | 3 | 3 | 3 | 3 | 3 | 3 | 3 | 3 |
|---|---|---|---|---|---|---|---|---|---|
| Isopropanol or ethyl alcohol | 17 | 27 | 42 | 3 | 11 | 45 | 3 | 3 | 3 |
| $CH_2Cl_2$ | | | 20 | 26 | 6 | 17 | 69 | 26 | 67 |
| Ethylglycol | | | | | | | | 2 | 2 |
| $CCl_3F+CCl_2F_2$ | 80 | 70 | | 68 | 80 | | | 66 | |
| Butane | | | 35 | | | 35 | 25 | | 25 |

TABLE 6

| Copolymer according to Example 3, 100% neutralized | 3 | 3 | 3 | 3 | 3 | 3 | 3 | 3 | 3 |
|---|---|---|---|---|---|---|---|---|---|
| Isopropanol or ethyl alcohol | 19 | 27 | 42 | 3 | 15 | 49 | 3 | 3 | 3 |
| $CH_2Cl_2$ | | | 20 | 26 | 6 | 18 | 69 | 26 | 67 |
| Ethylglycol | | | | | | | | 2 | 2 |
| $CCl_3F+CCl_2F_2$ | 78 | 70 | | 68 | 76 | | | 66 | |
| Butane | | | 35 | | | 30 | 25 | | 25 |

COMPARATIVE EXPERIMENT

Comparative measurements of the moisture absorption of four films were carried out in an atmosphere of 80% relative humidity. Three of the films were prepared from a copolymer according to the invention, described in Examples 1, 2 and 3 respectively. The fourth film consisted of a commercially available copolymer which was prepared in accordance with Example 3 of British Patent No. 1,041,910 and contained 84% of vinyl acetate, 8% of crotonic acid and 8% of the maleic acid half-ester of n-butanol.

Under equilibrium conditions, the percentage moisture absorption of the copolymers according to the invention, 100% neutralized with AMPD, was 9.7, 8.7 and 10.3% respectively whilst for the commercially available copolymer the moisture absorption was 13.8%. Hence, there was a 35% improvement in the hygroscopicity of the films. The results are summarized in Table 7.

TABLE 7

Water absorption of the films at 80% relative atmospheric humidity, as a function of the degree of neutralization

| | not neutralized | 50% neutralized with AMPD | 75% neutralized with AMPD | 100% neutralized with AMPD |
|---|---|---|---|---|
| 1st film[a] | | | | |
| after 3 days | 3.36% | 5.74% | 7.54% | 9.74% |
| after 7 days | 3.68% | 5.98% | 7.68% | 9.69% |
| 2nd film[b] | | | | |
| after 3 days | 2.97% | 4.59% | 6.35% | 8.14% |
| after 7 days | 3.23% | 4.87% | 6.64% | 8.72% |
| 3rd film[c] | | | | |
| after 3 days | 3.96% | 6.45% | 8.31% | 10.15% |
| after 7 days | 4.28% | 6.85% | 8.55% | 10.34% |
| 4th film[d] | | | | |
| after 3 days | 4.15% | 7.54% | 9.92% | 12.15% |
| after 7 days | 5.05% | 8.69% | 10.83% | 13.78% |

We claim:

1. A hair setting composition capable of producing a film on hair which can be washed off with water which comprises a 1 to 4% solution by weight of a water soluble polymeric resin in a solvent composed of one or more compounds selected from the group consisting of water and lower aliphatic alcohols wherein said resin is a copolymer of:
   a. from 20 to 95% by weight of at least one compound selected from the group consisting of vinyl esters of aliphatic carboxylic acids of 2 to 20 carbon atoms and esters of acrylic and methacrylic acid with aliphatic alcohols of 1 to 6 carbon atoms, and b. from 80 to 5% by weight of at least one compound selected from the group consisting of the half-esters of ethylenically unsaturated dibasic carboxylic acids of 4 to 5 carbon atoms with aliphatic alcohols of 6 to 24 carbon atoms;

which copolymer has been neutralized with from 10 to 150% by weight of the calculated theoretical amount of an inorganic or an organic base and wherein said copolymer, when measured as a 1% solution in isopropanol, has a relative viscosity of from 1.0 to 1.5.

2. The composition as set forth in claim 1 wherein said solvent is composed of one or more compounds selected from the group consisting of ethanol, isopropanol, and ethylglycol.

3. The composition as set forth in claim 1 wherein said copolymer contains from 30 to 85% by weight of component (a) and from 70 to 15% by weight of component (b).

4. The composition as set forth in claim 1 wherein component (a) consists of at least one compound selected from the group consisting of vinyl acetate, vinyl propionate, vinyl pivalate, vinyl esters of fatty acids of 10 to 20 carbon atoms, vinyl esters of branched carboxylic acids of 8 to 10 carbon atoms, and acrylic and methacrylic acid esters of isopropanol, isobutanol, tert.-butanol, and cyclohexanol; and wherein component (b) consists of at least one compound selected from the group consisting of the half-esters of maleic, fumaric, citraconic, mesaconic and itaconic acids with cyclohexanol and fatty alcohols of 10 to 20 carbon atoms.

5. The composition as set forth in claim 1 wherein said copolymer has been neutralized with an organic base selected from the group consisting of ammonia, diethylamine, dimethylamine, triethanolamine, triisopropanolamine, 2-amino-2-methanolpropanol, and 1,2-amino-2-methyl-1,3-propanediol.

6. The composition as set forth in claim 1 wherein said copolymer additionally contains up to 10%, based on the weight of the copolymer, of copolymerized units selected from the group consisting of diethylaminoethyl acrylate, diethylaminoethyl methacrylate, dimethylaminoethyl acrylate, dimethylaminoethyl methacrylate, and vinylimidazole.

7. The composition as set forth in claim 1 wherein the solvent additionally contains a halogenated hydrocarbon propellant gas.

8. The composition as set forth in claim 7 wherein the solvent is selected from the group consisting of ethanol and isopropanol and wherein from 40 to 75% by weight of propellant gas is present based on the combined amount of solvent, and propellant.

9. The composition as set forth in claim 1 wherein said solvent is 20 to 50% aqueous ethanol or isopropanol solution.

10. The composition as set forth in claim 1 wherein component (a) consists of at least one compound selected from the group consisting of vinyl acetate, methyl acrylate, and methyl methacrylate; and wherein component (b) consists of at least one compound selected from the group consisting of the maleic acid half-esters of cyclohexanol and an alcohol fraction of from 12 to 14 carbon atoms.

* * * * *